United States Patent
Hendricks

(10) Patent No.: US 12,302,815 B1
(45) Date of Patent: May 20, 2025

(54) ONION HYBRID SVNT4677

(71) Applicant: Seminis Vegetable Seeds, Inc., St. Louis, MO (US)

(72) Inventor: Jeffery Scott Hendricks, Sun Prairie, WI (US)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 0 days.

(21) Appl. No.: 18/959,386

(22) Filed: Nov. 25, 2024

(51) Int. Cl.
*A01H 5/10* (2018.01)
*A01H 6/04* (2018.01)

(52) U.S. Cl.
CPC .............. *A01H 6/045* (2018.05); *A01H 5/10* (2013.01)

(58) Field of Classification Search
None
See application file for complete search history.

(56) References Cited

U.S. PATENT DOCUMENTS 9,516,851 B2 * 12/2016 Bowman ................. A01H 5/04

OTHER PUBLICATIONS

U.S. Appl. No. 18/960,768, filed Nov. 26, 2024, Hendricks.
Larkin et al., "Somaclonal variation—a novel source of variability from cell cultures for plant improvement," *Theor Appl Genet*, 60(4):197-214; 1981.
Moose et al., "Molecular plant breeding as the foundation for 21st century crop improvement," *Plant Physiol*, 147(3):969-77, 2008.
Chandel, et al. "Screening of short-day onions for resistance to Stemphylium leaf blight in the seed-to-bulb stage (stage I) and bulb-to-seed stage (stage II)." Front. Plant Sci. Vol. 13, (2022).
Finkers, et al. "Insights from the first genome assembly of Onion (*Allium cepa*)." G3 (Genes|Genomes|Genetics, vol. 11 (9), (2021).
Hay, et al. "Stemphylium Leaf Blight: A Re-Emerging Threat to Onion Production in Eastern North America." Plant Disease, vol. 105 (12), pp. 3780-3794, (2021).

* cited by examiner

*Primary Examiner* — Jason Deveau Rosen
(74) *Attorney, Agent, or Firm* — Dentons US LLP

(57) ABSTRACT

The invention provides seeds and plants of the onion hybrid designated SVNT4677. The invention thus relates to the plants, seeds and tissue cultures of onion hybrid SVNT4677, and to methods for producing an onion plant produced by crossing such plants with themselves or with another onion plant, such as an onion plant of another genotype. The invention further relates to seeds and plants produced by such crossing. The invention further relates to plants, seeds, plant parts, and tissue cultures of onion hybrid SVNT4677 comprising introduced beneficial or desirable traits, including the bulbs and gametes of such plants.

27 Claims, No Drawings

ONION HYBRID SVNT4677

FIELD OF THE INVENTION

The present invention relates to the field of plant breeding and, more specifically, to the development of onion hybrid SVNT4677.

BACKGROUND OF THE INVENTION

The goal of vegetable breeding is to combine various desirable traits in a single variety. Such desirable traits may include any trait deemed beneficial or desirable by a grower or consumer, including greater yield, resistance to insects or disease, tolerance to environmental stress, and nutritional value.

Breeding techniques take advantage of a plant's method of pollination. There are two general methods of pollination: a plant self-pollinates if pollen from plant is transferred to a flower of the same plant or to a flower of another plant of the same genotype. A plant cross-pollinates if pollen comes to it from a flower of a plant of a different genotype.

Plants that have been self-pollinated and selected for type over many generations become homozygous at almost all genetic loci and produce a uniform population of true breeding progeny, a homozygous plant. A cross between two such homozygous plants of different genotypes produces a uniform population of hybrid plants that are heterozygous for many genetic loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines and hybrids derived therefrom are developed by selfing and selection of desired phenotypes. The new lines and hybrids are evaluated to determine which of those have commercial potential.

One breeding technique of value for use in onions is use of "dihaploid" breeding. This technique involves doubling the chromosome number of a haploid derived from a starting heterozygous plant in order to recover a progeny dihaploid plant that is homozygous, with both sets of chromosomes being recovered from the haploid in the case of a diploid species. Polyploids may also be obtained using this method.

One crop species which has been subject to such breeding programs and is of particular value is onion. Onions belong to the lily family, Amaryllidaceae, and the genus, *Allium*. This genus comprises a group of perennial herbs having bulbous, onion-scented underground leaves, including such commonly cultivated crops as onion, garlic, chives, shallots and leeks. It also includes ornamental species grown for their flowers.

Onions are an important vegetable world-wide, ranking second among all vegetables in economic importance with an estimated value of $6 billion dollars annually. The onion is also one of the oldest cultivated vegetables. Common bulbing onions are of the species *Allium cepa*. Onions are classified in numerous ways, by basic use, flavor, color, shape of the bulb, and day length. Onions come in white, yellow, and red colors. The bulb may be rounded, flattened, or torpedo shaped.

Commercial onions include "storage onions", "fresh onions", "pearl or mini onions", and "green bunching onions." Green bunching onions, also called Welsh onions or Japanese bunching onions, are young onion plants that are harvested with the green tops attached and are used both fresh and as a cooked ingredient. They are mild in flavor and are used frequently in salads. These are typically of the species *Allium fistulosum*. Green bunching onions are available in the United States during the entire year.

Onions are most frequently grown from seed. A small fraction of the crop is grown from transplants or "sets." Onion sets are produced by sowing seed very thickly one year, resulting in small bulbs that that are easily set out and grown into mature bulbs the next year. Onion transplants are seedlings that are sown thickly and grown without bulbing for 45-90 days. These plants are then harvested and trimmed and replanted at lower populations in the final fields for bulb production. While breeding efforts to date have provided a number of useful onion lines with beneficial traits, there remains a great need in the art for new lines with further improved traits. Such plants would benefit farmers and consumers alike by improving crop yields or quality.

SUMMARY OF THE INVENTION

In one aspect, the present invention provides an onion plant of the onion hybrid designated SVNT4677. Also provided are onion plants having all the physiological and morphological characteristics of such a plant. Parts of the onion plant of the present invention are also provided, for example, including pollen, an ovule, an embryo, a seed, a scion, a rootstock, a bulb, and a cell of the plant.

The invention also concerns seed of onion hybrid SVNT4677. The onion seed of the invention may be provided, in certain illustrative embodiments, as an essentially homogeneous population of onion seed of the hybrid designated SVNT4677. Essentially homogeneous populations of seed are generally free from substantial numbers of other seed. Therefore, in one embodiment, seed of hybrid SVNT4677 may be defined as forming at least about 90% of the total seed, including at least about 91%, 92%, 93%, 94%, 95%, 96%, 97%, 98%, 99%, or more of the seed. The seed population may be separately grown to provide an essentially homogeneous population of onion plants designated SVNT4677.

In another aspect of the invention, a plant of onion hybrid SVNT4677 comprising an added heritable trait is provided. The heritable trait may comprise a genetic locus that is, for example, a dominant or recessive allele. In one embodiment of the invention, a plant of onion hybrid SVNT4677 is defined as comprising a single locus conversion. In specific embodiments of the invention, an added genetic locus confers one or more traits such as, for example, herbicide tolerance, insect resistance, disease resistance, and modified carbohydrate metabolism. In further embodiments, the trait may be conferred by a naturally occurring gene introduced into the genome of a line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

In some embodiments, a single locus conversion includes one or more site-specific changes to the plant genome, such as, without limitation, one or more nucleotide modifications, deletions, or insertions. A single locus may comprise one or more genes or nucleotides integrated or mutated at a single chromosomal location. In one embodiment, a single locus conversion may be introduced by a genetic engineering technique, methods of which include, for example, genome editing with engineered nucleases (GEEN). Engineered nucleases include, but are not limited to, Cas endonucleases; zinc finger nucleases (ZFNs); transcription activator-like effector nucleases (TALENs); engineered meganucleases, also known as homing endonucleases; and other endonucleases for DNA or RNA-guided genome editing that are well-known to the skilled artisan.

In another aspect of the invention, a tissue culture of regenerable cells of a plant of hybrid SVNT4677 is provided. The tissue culture will preferably be capable of regenerating onion plants capable of expressing all of the physiological and morphological characteristics of the starting plant, and of regenerating plants having substantially the same genotype as the starting plant. Examples of some of the physiological and morphological characteristics of the hybrid SVNT4677 include those traits set forth in the table herein. The regenerable cells in such tissue cultures may be derived, for example, from embryos, meristems, cotyledons, pollen, leaves, anthers, roots, root tips, pistils, flowers, seeds and stalks. Still further, the present invention provides onion plants regenerated from a tissue culture of the invention, the plants having all the physiological and morphological characteristics of hybrid SVNT4677.

In yet another aspect of the invention, processes are provided for producing onion seeds, plants, parts thereof, and bulbs, which processes generally comprise crossing a first parent onion plant with a second parent onion plant, wherein at least one of the first or second parent onion plants is a plant of the hybrid designated SVNT4677 or a progeny plant thereof. In one embodiment, the present invention provides a method for producing onion seeds, plants, and parts thereof, which comprise selfing onion hybrid SVNT4677 or a progeny plant thereof. These processes may be further exemplified as processes for preparing hybrid onion seed or plants, wherein a first onion plant is crossed with a second onion plant of a different, distinct genotype to provide a hybrid that has, as one of its parents, an inbred onion plant derived from onion hybrid SVNT4677. In these processes, crossing or selfing will result in the production of seed. The seed production occurs regardless of whether the seed is collected or not. The present invention also provides the onion seeds and plants produced by a process that comprises crossing a first parent onion plant with a second parent onion plant, or by self-pollination of a first parent onion plant or a second parent onion plant, wherein at least one of the first or second parent onion plants is a plant of onion hybrid SVNT4677 or a progeny plant thereof. In one embodiment of the invention, onion seed and plants produced by the process are first generation (F1) hybrid onion seed and plants produced by crossing a plant in accordance with the invention with another, distinct plant. The present invention further contemplates plant parts of such an F1 hybrid onion plant, and methods of use thereof. Therefore, certain exemplary embodiments of the invention provide an F1 hybrid onion plant and seed thereof.

In one embodiment of the invention, the first step in "crossing" comprises planting seeds of a first and second parent onion plant, often in proximity so that pollination will occur for example, mediated by insect vectors. In certain embodiments, where the first and second parent plant are plants of the same genotype, the crossing of the first and second parent plant may be referred to as selfing or self-pollinating. Alternatively, pollen can be transferred manually. Where the plant is self-pollinated, pollination may occur without the need for direct human intervention other than plant cultivation.

A second step may comprise cultivating or growing the seeds of first and second parent onion plants into plants that bear flowers. A third step may comprise preventing self-pollination of the plants, such as by emasculating the flowers, (i.e., killing or removing pollen).

A fourth step for a hybrid cross may comprise cross-pollination between the first and second parent onion plants. Yet another step comprises harvesting the seeds from at least one of the parent onion plants. The harvested seed can be grown to produce an onion plant or hybrid onion plant.

In still yet another aspect of the invention, the genetic complement of onion hybrid SVNT4677 is provided. The phrase "genetic complement" is used to refer to the aggregate of nucleotide sequences, the expression of which sequences defines the phenotype of, in the present case, an onion plant, or a cell or tissue of that plant. A genetic complement thus represents the genetic makeup of a cell, tissue or plant, and a hybrid genetic complement represents the genetic make up of a hybrid cell, tissue or plant. The invention thus provides onion plant cells that have a genetic complement in accordance with the onion plant cells disclosed herein, and seeds and plants containing such cells.

Plant genetic complements may be assessed by genetic marker profiles, and by the expression of phenotypic traits that are characteristic of the expression of the genetic complement, e.g., isozyme typing profiles. It is understood that onion hybrid SVNT4677 could be identified by any of the many well known techniques such as, for example, Simple Sequence Length Polymorphisms (SSLPs) (Williams et al., *Nucleic Acids Res.*, 1 8:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science*, 280:1077-1082, 1998).

In still yet another aspect, the present invention provides hybrid genetic complements, as represented by onion plant cells, tissues, plants, and seeds, formed by the combination of a haploid genetic complement of an onion plant of the invention with a haploid genetic complement of a second onion plant, preferably, another, distinct onion plant. In another aspect, the present invention provides an onion plant regenerated from a tissue culture that comprises a hybrid genetic complement of this invention.

In still yet another aspect, the invention provides a method of determining the genotype of a plant comprising at least a first set of chromosomes of onion hybrid SVNT4677 or a progeny plant thereof, or a part thereof, the method comprising detecting at least a first polymorphism in a sample of nucleic acids from the plant or part thereof. In one embodiment, the detecting comprises DNA sequencing or genetic marker analysis. In yet another embodiment, the present invention provides a method of determining the genotype of a plant comprising at least a first set of chromosomes of onion hybrid SVNT4677, or a progeny plant thereof, or a part thereof, the method comprising detecting at least a first polymorphism in a set of the chromosomes of onion hybrid SVNT4677 or progeny thereof. In one embodiment, the present invention provides a method of determining the genotype of a plant comprising at least a first set of chromosomes of onion hybrid SVNT4677 or a progeny plant thereof, or a part thereof, the method comprising comparing at least a first nucleotide sequence obtained from the plant or part thereof to at least a first reference nucleotide sequence obtained from a reference plant; and detecting at least one polymorphism between the first nucleotide sequence and the first reference sequence. The methods of the present invention may, in certain embodiments, comprise detecting a plurality of polymorphisms in a sample of nucleic acids as described herein. The method may further, in some embodiments, comprise storing the results of the step of detecting the at least one polymorphism or the plurality of polymorphisms on a computer readable medium, or transmitting the results of detecting the at least one polymorphism or the plurality of polymorphisms. The present invention, in particular embodiments, further provides a computer readable medium produced by the methods of the present invention.

In still yet another aspect, the present invention provides a method of producing a plant derived from onion hybrid SVNT4677, the method comprising the steps of: (a) preparing a progeny plant derived from onion hybrid SVNT4677, wherein said preparing comprises crossing a plant of onion hybrid SVNT4677 with itself or a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from onion hybrid SVNT4677. In certain embodiments, the crossing of a plant with itself may be referred to as selfing or self-pollination. The plant derived from onion hybrid SVNT4677 may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from onion hybrid SVNT4677 is obtained which possesses some of the desirable traits of the line as well as potentially other selected traits.

In certain embodiments, the present invention provides a method of producing onion comprising: (a) obtaining a plant of onion hybrid SVNT4677, wherein the plant has been cultivated to maturity, and (b) collecting onions from the plant.

In another aspect, the present invention provides an onion plant comprising a *Stemphylium* leaf blight (SLB) resistance allele that confers to the plant an increased resistance to SLB compared to a plant not comprising the allele, wherein the allele is inherited from a plant of onion hybrid SVNT4677 or a progeny plant thereof. In one embodiment, the plant is a hybrid onion plant. In another embodiment, the plant is an inbred onion plant. In yet another embodiment, the present invention provides an onion seed that produces an onion plant comprising a *Stemphylium* leaf blight (SLB) resistance allele that confers to the plant an increased resistance to SLB compared to a plant not comprising the allele, wherein the allele is inherited from a plant of onion hybrid SVNT4677 or a progeny plant thereof. The present invention, in some embodiments, provides a plant parts or tissue cultures of regenerable cells of onion plants comprising a *Stemphylium* leaf blight (SLB) resistance allele that confers to the plant an increased resistance to SLB compared to a plant not comprising the allele, wherein the allele is inherited from a plant of onion hybrid SVNT4677 or a progeny plant thereof.

Any embodiment discussed herein with respect to one aspect of the invention applies to other aspects of the invention as well, unless specifically noted.

The term "about" is used to indicate that a value includes the standard deviation of the mean for the device or method being employed to determine the value. The use of the term "or" in the claims is used to mean "and/or" unless explicitly indicated to refer to alternatives only or the alternatives are mutually exclusive. When used in conjunction with the word "comprising" or other open language in the claims, the words "a" and "an" denote "one or more," unless specifically noted otherwise. The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has," or "includes" one or more steps is not limited to possessing only those one or more steps and also covers other unlisted steps. Similarly, any plant that "comprises," "has," or "includes" one or more traits is not limited to possessing only those one or more traits and covers other unlisted traits.

Other objects, features, and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from the detailed description.

DETAILED DESCRIPTION OF THE INVENTION

The present invention provides methods and compositions relating to plants, seeds, and derivatives of onion hybrid SVNT4677. Onion hybrid SVNT4677, also known 18-SL-OLR-4677, is an early season red onion variety that has a uniform shape. The hybrid is suitable for medium to long term storage and comprises a trait conferring broad-spectrum resistance to *Stemphylium vesicarium*.

A. ORIGIN AND BREEDING HISTORY OF ONION HYBRID SVNT4677

The parents of onion hybrid SVNT4677 are (i) an early maturity, long day, red onion line with medium pungency levels, a medium bulb size, and a high globe shape; and (ii) a long day, red onion line with low pungency levels and resistance to *Stemphylium vesicarium*. The parent lines are uniform and stable, as is a hybrid produced therefrom. A small percentage of variants can occur within commercially acceptable limits for almost any characteristic during the course of repeated multiplication. However, no variants are expected.

B. PHYSIOLOGICAL AND MORPHOLOGICAL CHARACTERISTICS OF ONION HYBRID SVNT4677

In accordance with one aspect of the present invention, there are provided plants having the physiological and morphological characteristics of onion hybrid SVNT4677.

Descriptions of the physiological and morphological characteristics of onion hybrid SVNT4677 are presented in the table that follows.

TABLE 1

Physiological and Morphological Characteristics of Onion Hybrid SVNT4677

| CHARACTERISTIC | SVNT4677 |
|---|---|
| Type | |
| type | bulb |
| type | long day |
| adaption range (degrees mean latitude) | 38 to 46 |
| maturity (days) | early (75-90) |
| Plant | |
| height (cm) (above soil line to the highest point of any foliage) | 50 |
| number of cm shorter than comparable variety | 5 |
| attitude | intermediate/floppy |
| number of leaves per pseudostem | many |
| male sterility | strong (81%-100%) |
| Foliage | |
| attitude | semi-erect |
| waxiness | weak |
| intensity of green color | light green |
| cranking | intermediate |
| Leaf | |
| length | medium |
| length (before maturity yellowing begins) (cm) | 35 |
| diameter | medium |
| width (mm) | 12 |
| leaf thickness (mm) (at mid-length of longest leaf) | 8 |
| Pseudostem | |
| length (up to the highest green leaf) | medium |
| diameter (at midpoint of length) | medium |
| Sheath | |
| scape length (from soil line to base of inflorescence) (cm) | 120 |
| Inflorescence | |
| maximum number per plant | 3 |
| minimum number per plant | 1 |
| type | loose/open |
| spathe | short beak |
| flower color | green |
| anther color | light green |
| pollen viability | sterile |
| Bulb | |
| average number of bulbs per meter | 14 |
| tendency to split in bulblets (with dry skin around each bulblet) | absent or very weak |
| size (at harvest) | medium |
| height | medium |
| diameter | medium |
| ratio height/diameter | medium |
| position of maximum diameter | toward stem end |
| width of neck | broad |
| shape (in longitudinal section) | broad obovate |
| shape of stem end | slightly raised |
| shape of root end | weakly tapered |
| adherence of dry skin after harvest | medium |
| thickness of dry skin | thin |
| base color of dry skin | red |
| intensity of base color of dry skin | dark |
| hue of color of dry skin (in addition to base color) | purplish |
| coloration of epidermis of fleshy scales | reddish |

TABLE 1-continued

Physiological and Morphological Characteristics of Onion Hybrid SVNT4677

| CHARACTERISTIC | SVNT4677 |
|---|---|
| number of growing points per kg | low |
| dry matter content | low |
| shape | top shape |
| skin color | purplish red |
| interior color | purplish red |
| scales | few |
| scale retention | good |
| pungency | mild |
| storage | good |
| tendency to bolting in spring sown trials | weak |
| time of beginning of bolting in spring sown trials | late |
| time of harvest maturity for spring sown trials | early |
| time of sprouting during storage | medium |

*These are typical values. Values may vary due to environment. Values that are substantially equivalent are within the scope of the invention.

C. BREEDING ONION PLANTS

One aspect of the current invention concerns methods for producing a seed of onion hybrid SVNT4677 involving crossing (i) an early maturity, long day, red onion line with medium pungency levels, a medium bulb size, and a high globe shape; and (ii) a long day, red onion line with low pungency levels and resistance to *Stemphylium vesicarium*. Alternatively, in other embodiments of the invention, onion hybrid SVNT4677 or a progeny plant thereof may be crossed with itself or with any second plant. In one embodiment, the crossing of a plant with itself may be referred to as selfing or self-pollination. Such methods can be used for propagation of hybrid SVNT4677 or can be used to produce plants derived from hybrid SVNT4677. Plants derived from onion hybrid SVNT4677 or progeny thereof may be used, in certain embodiments, for the development of new onion varieties.

The development of new varieties using one or more starting varieties is well known in the art. In accordance with the invention, novel varieties may be created by crossing hybrid SVNT4677 or progeny thereof followed by multiple generations of breeding according to such well-known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) in progeny or when in hybrid combination. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner, true breeding lines can be produced in as little as one generation. Haploid embryos may be produced from microspores, pollen, anther cultures, or ovary cultures. The haploid embryos may then be doubled autonomously, or by chemical treatments (e.g., colchicine treatment). Alternatively, haploid embryos may be grown into haploid plants and treated to induce chromosome doubling. In either case, fertile homozygous plants are obtained. In accordance with the invention, any of such techniques may be used in connection with a plant of the invention and progeny thereof to achieve a homozygous line.

New varieties may be created, for example, by crossing hybrid SVNT4677 with any second plant and selection of progeny in various generations or by doubled haploid technology. In choosing a second plant to cross for the purpose of developing novel lines, it may be desired to choose those plants which either themselves exhibit one or more selected desirable characteristics or which exhibit the desired characteristic(s) in progeny. After one or more lines are crossed, true-breeding lines may be developed.

Backcrossing can also be used to improve an inbred plant. Backcrossing transfers a specific desirable trait from one inbred or non-inbred source to an inbred that lacks that trait. This can be accomplished, for example, by first crossing a superior inbred (recurrent parent) to a donor inbred (non-recurrent parent), which carries the appropriate locus or loci for the trait in question. The progeny of this cross are then mated back to the superior recurrent parent followed by selection in the resultant progeny for the desired trait to be transferred from the non-recurrent parent. After five or more backcross generations with selection for the desired trait, the progeny have the characteristic being transferred, but are like the superior recurrent parent for most or almost all other loci. The last backcross generation would be selfed to give pure breeding progeny for the trait being transferred.

The plants of the present invention are particularly well suited for the development of new lines based on the elite nature of the genetic background of the plants. In selecting a second plant to cross with SVNT4677 for the purpose of developing novel onion lines, it will typically be preferred to choose those plants which either themselves exhibit one or more selected desirable characteristics or which exhibit the desired characteristic(s) when in hybrid combination. Examples of desirable characteristics may include, but are not necessarily limited to, enhanced flavor; reduced flavor; low pungency (such producing a bulb having a pyruvic acid development (PAD) measurement of less than 5.5 µM/g FW of pyruvate, for example); increased resistance to viral pathogens, for example, iris yellow spot virus, onion yellow dwarf virus, onion mosaic virus, and onion mite-borne latent virus; increased resistance to one or more bacterial pathogens, for example, *Erwinia carotovora* ssp. *carotovora, E. chrysanthemi, Pseudomonas gladioli,* and *Enterobacter cloacae,* such as are related to bacterial soft rot, onion bacterial blight, caused by *Xanthomonas* sp; increased resistance to one or more fungal diseases, such as purple blotch, caused by the fungus *Alternaria porri,* downy mildew, caused by the fungus *Peronospora destructor; Botrytis* leaf blight (Blast) symptoms, caused by *Botrytis* spp.; white rot, caused by *Fusarium;* and *Botrytis* neck rot; increased resistance to insects (e.g. bulb mites; maggots; pea leafminer; *thrips*; wheat curl mite; and onion eelworm); and the like.

Furthermore, examples of desirable characteristics may also include, in specific embodiments, high seed yield, high seed germination, seedling vigor, high bulb yield, disease tolerance or resistance, and adaptability for soil and climate conditions. Consumer-driven traits, such as bulb shape, color, texture, and taste are other examples of traits that may be incorporated into new lines of onion plants developed by this invention.

D. FURTHER EMBODIMENTS OF THE INVENTION

In certain aspects of the invention, plants described herein are provided modified to include at least a first desired heritable trait. Such plants may, in one embodiment, be developed by a plant breeding technique called backcrossing, wherein essentially all of the physiological and morphological characteristics of a variety are recovered in addition to a genetic locus transferred into the plant via the backcrossing technique. The term single locus converted plant as used herein refers to those onion plants which are developed by a plant breeding technique called backcrossing or by genetic engineering, wherein essentially all of the desired physiological and morphological characteristics of a variety are recovered or conserved in addition to the single locus introduced into the variety via the backcrossing or genetic engineering technique, respectively. By essentially all of the morphological and physiological characteristics, it is meant that the characteristics of a plant are recovered or conserved that are otherwise present when compared in the same environment, other than an occasional variant trait that might arise during backcrossing, introduction of a transgene, or application of a genetic engineering technique.

Backcrossing methods can be used with the present invention to improve or introduce a characteristic into the present variety. The parental onion plant which contributes the locus for the desired characteristic is termed the nonrecurrent or donor parent. This terminology refers to the fact that the nonrecurrent parent is used one time in the backcross protocol and therefore does not recur. The parental onion plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until an onion plant is obtained wherein essentially all of the desired physiological and morphological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele, or an additive allele (between recessive and dominant), may also be transferred. In this instance it may be necessary to introduce a test of the progeny to determine if the desired characteristic has been successfully transferred.

In one embodiment, progeny onion plants of a backcross in which a plant described herein is the recurrent parent comprise (i) the desired trait from the non-recurrent parent and (ii) all of the physiological and morphological characteristics of onion recurrent parent as determined at the 5% significance level when grown in the same environmental conditions.

New varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

With the development of molecular markers associated with particular traits, it is possible to add additional traits into an established germ line, such as represented here, with the end result being substantially the same base germplasm with the addition of a new trait or traits. Molecular breeding, as described in Moose and Mumm, 2008 (*Plant Physiology*, 147:969-977), for example, and elsewhere, provides a mechanism for integrating single or multiple traits or QTL into an elite line. This molecular breeding-facilitated movement of a trait or traits into an elite line may encompass incorporation of a particular genomic fragment associated with a particular trait of interest into the elite line by the mechanism of identification of the integrated genomic fragment with the use of flanking or associated marker assays. In the embodiment represented here, one, two, three or four genomic loci, for example, may be integrated into an elite line via this methodology. When this elite line containing the additional loci is further crossed with another parental elite line to produce hybrid offspring, it is possible to then incorporate at least eight separate additional loci into the hybrid. These additional loci may confer, for example, such traits as a disease resistance or a bulb quality trait. In one embodiment, each locus may confer a separate trait. In another embodiment, loci may need to be homozygous and exist in each parent line to confer a trait in the hybrid. In yet another embodiment, multiple loci may be combined to confer a single robust phenotype of a desired trait.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, modified fatty acid or carbohydrate metabolism, and altered nutritional quality. These comprise genes generally inherited through the nucleus.

Direct selection may be applied where the single locus acts as a dominant trait. For this selection process, the progeny of the initial cross are assayed for viral resistance or the presence of the corresponding gene prior to the backcrossing. Selection eliminates any plants that do not have the desired gene and resistance trait, and only those plants that have the trait are used in the subsequent backcross. This process is then repeated for all additional backcross generations.

Selection of onion plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait in a plant can also be useful for breeding purposes. Procedures for marker assisted selection applicable to the breeding of onion are well known in the art. Such methods will be of particular utility in the case of recessive traits and variable phenotypes, or where conventional assays may be more expensive, time consuming or otherwise disadvantageous. In addition, marker assisted selection may be used to identify plants comprising desirable genotypes at the seed, seedling, or plant stage, to identify or assess the purity of a cultivar, to catalog the genetic diversity of a germplasm collection, and to monitor specific alleles or haplotypes within an established cultivar.

Types of genetic markers which could be used in accordance with the invention include, but are not necessarily limited to, Simple Sequence Length Polymorphisms (SSLPs) (Williams et al., *Nucleic Acids Res.*, 1 8:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science*, 280:1077-1082, 1998).

In particular embodiments of the invention, marker assisted selection is used to increase the efficiency of a backcrossing breeding scheme for producing an onion line comprising a desired trait. This technique is commonly referred to as marker assisted backcrossing (MABC). This technique is well-known in the art and may involve, for example, the use of three or more levels of selection, including foreground selection to identity the presence of a desired locus, which may complement or replace phenotype screening protocols; recombinant selection to minimize linkage drag; and background selection to maximize recurrent parent genome recovery.

E. PLANTS DERIVED BY GENETIC ENGINEERING

Various genetic engineering or gene editing technologies have been developed and may be used by those of skill in the art to introduce traits in plants. In certain aspects of the claimed invention, traits are introduced into onion plants via altering or introducing a single genetic locus, site-specific modification, or transgene into the genome of a recited variety or progenitor thereof. Methods of genetic engineering to modify, delete, or insert genes and polynucleotides into the genomic DNA of plants are well-known in the art.

In specific embodiments of the invention, improved onion lines can be created through the site-specific modification of a plant genome. In certain embodiments, a site-specific modification may be referred to as a gene edit. Methods of genetic engineering to introduce a site-specific modification include, for example, utilizing sequence-specific nucleases such as zinc-finger nucleases (see, for example, U.S. Pat. Appl. Pub. No. 2011-0203012); engineered or native meganucleases; TALE-endonucleases (see, for example, U.S. Pat. Nos. 8,586,363 and 9,181,535); and RNA-guided endonucleases, such as those of the CRISPR/Cas systems (see, for example, U.S. Pat. Nos. 8,697,359, 8,771,945, and 10,266, 850). One embodiment of the invention thus relates to utilizing a nuclease or any associated protein to carry out genome modification. This nuclease could be provided heterologously within donor template DNA for templated-genomic editing or in a separate molecule or vector. A recombinant DNA construct may also comprise a sequence encoding one or more guide RNAs to direct the nuclease to the site within the plant genome to be modified. Further methods for altering or introducing a single genetic locus include, for example, utilizing single-stranded oligonucleotides to introduce base pair modifications in an onion plant genome (see, for example Sauer et al., *Plant Physiol*, 170 (4): 1917-1928, 2016).

Methods for site-directed alteration or introduction of a single genetic locus are well-known in the art and include those that utilize sequence-specific nucleases, such as the aforementioned, or complexes of proteins and guide-RNA that cut genomic DNA to produce a double-strand break (DSB) or nick at a genetic locus. In certain embodiments, methods for producing a site-directed alteration may be referred to as gene-editing. As is well-understood in the art, during the process of repairing the DSB or nick introduced by the nuclease enzyme, a donor template, transgene, or expression cassette polynucleotide may become integrated into the genome at the site of the DSB or nick. The presence of homology arms in the DNA to be integrated may promote the adoption and targeting of the insertion sequence into the plant genome during the repair process through homologous recombination or non-homologous end joining (NHEJ).

In another embodiment of the invention, genetic transformation may be used to insert a selected transgene into a plant of the invention or may, alternatively, be used for the preparation of transgenes which can be introduced by backcrossing. Methods for the transformation of plants that are well known to those of skill in the art and applicable to many crop species include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

Many useful traits are those which are introduced by genetic transformation techniques. Methods for the genetic transformation of onion are known to those of skill in the art. For example, methods which have been described for the genetic transformation of onion may include electroporation, electrotransformation, microprojectile bombardment, *Agrobacterium*-mediated transformation, direct DNA uptake transformation of protoplasts and silicon carbide fiber-mediated transformation. See, e.g., Khachatourians et al., (In: *Transgenic Plants and Crops*, Marcel Dekker, Inc., 2002)

It is understood to those of skill in the art that a transgene need not be directly transformed into a plant, as techniques for the production of stably transformed onion plants that pass single loci to progeny by Mendelian inheritance is well known in the art. Such loci may therefore be passed from parent plant to progeny plants by standard plant breeding techniques that are well known in the art. Examples of traits that may be introduced into an onion plant according to the invention include, for example, male sterility, herbicide resistance, disease resistance, insect resistance, and enhanced nutritional quality.

PCR and Southern hybridization are two examples of molecular techniques that can be used for confirmation of the presence of a given locus and thus conversion of that locus.

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target onion cells. The screen disperses the particles so that they are not delivered to the recipient cells in large aggregates. Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., *Nat. Biotechnol*, 3 (7): 637-642, 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., *Nat. Biotechnol.*, 3:629-635, 1985; U.S. Pat. No. 5,563,055). One example of an onion transformation protocol for *Agrobacterium tumefaciens*-mediated transformation involves use of immature embryos as an explant source (Eady et al., *Plant Cell Rep.*, 19:376-381, 2000). Multiple-shoot formation from primary transgenic material made possible the clonal multiplication of transformants.

Transformation of plant protoplasts also can be achieved using methods based on calcium phosphate precipitation, polyethylene glycol treatment, electroporation, and combinations of these treatments (see, e.g., Potrykus et al., *Mol. Gen. Genet.*, 199:183-188, 1985; Omirulleh et al., *Plant Mol. Biol.*, 21 (3): 415-428, 1993; Fromm et al., *Nature*, 312:791-793, 1986; Uchimiya et al., *Mol. Gen. Genet.*, 204:204, 1986; Marcotte et al., *Nature*, 335:454, 1988). Transformation of plants and expression of foreign genetic elements is exemplified in Choi et al. (*Plant Cell Rep.*, 13:344-348, 1994), and Ellul et al. (*Theor. Appl. Genet.*, 107:462-469, 2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for plant gene expression include, but are not limited to, the cauliflower mosaic virus (CaMV) P-35S promoter, which confers constitutive, high-level expression in most plant tissues (see, e.g., Odel et al., *Nature*, 313:810, 1985), including in monocots (see, e.g., Dekeyser et al., *Plant Cell*, 2:591, 1990; Terada and Shimamoto, *Mol. Gen. Genet.*, 220:389, 1990); a tandemly duplicated version of the CaMV 35S promoter, the enhanced 35S promoter (P-e35S) the nopaline synthase promoter (An et al., *Plant Physiol.*, 88:547, 1988), the octopine synthase promoter (Fromm et al., *Plant Cell*, 1:977, 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem, the cauliflower mosaic virus 19S promoter, a sugarcane bacilliform virus promoter, a *commelina* yellow mottle virus promoter, and other plant DNA virus promoters known to express in plant cells.

A variety of plant gene promoters that are regulated in response to environmental, hormonal, chemical, or developmental signals can also be used for expression of an operably linked gene in plant cells, including promoters regulated by (1) heat (Callis et al., *Plant Physiol.*, 88:965, 1988), (2) light (e.g., pea rbcS-3A promoter, Kuhlemeier et al., *Plant Cell*, 1:471, 1989; maize rbcS promoter, Schaffner and Sheen, *Plant Cell*, 3:997, 1991; or chlorophyll a/b-binding protein promoter, Simpson et al., *EMBO J.*, 4:2723, 1985), (3) hormones, such as abscisic acid (Marcotte et al., *Plant Cell*, 1:969, 1989), (4) wounding (e.g., wun1, Siebertz et al., *Plant Cell*, 1:961, 1989); or (5) chemicals such as methyl jasmonate, salicylic acid, or Safener. It may also be advantageous to employ organ-specific promoters (e.g., Roshal et al., *EMBO J.*, 6:1155, 1987; Schernthaner et al., *EMBO J.*, 7:1249, 1988; Bustos et al., *Plant Cell*, 1:839, 1989).

Exemplary nucleic acids which may be introduced to plants of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into an onion plant according to the invention. Non-limiting examples of particular genes and corresponding phenotypes one may choose to introduce into an onion plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference in their entirety. In another embodiment, the structural gene can confer tolerance to the herbicide glyphosate as conferred by genes including, but not limited to *Agrobacterium* strain CP4 glyphosate resistant EPSPS gene (aroA: CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., *Biotech. Gen. Engin. Rev.*, 9:207, 1991). The RNA could also be a catalytic RNA molecule (i.e., a ribozyme) engineered to cleave a desired endogenous mRNA product (see for example, Gibson and Shillito, *Mol. Biotech.*, 7:125, 1997). Thus, any gene which produces a protein or mRNA which expresses a phenotype or morphology change of interest is useful for the practice of the present invention.

F. GENOTYPING

In certain aspects of the present invention, the genotype or genetic fingerprint of a plant may be examined. There are many laboratory-based techniques available to those of ordinary skill in the art for the determination, analysis, comparison, and characterization of a plant genotype or genetic fingerprint. Non-limiting examples of such techniques include Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), and Single Nucleotide Polymorphisms (SNPs). In certain embodiments, sequence-based methods may utilize SNPs that are randomly distributed across the genome of a particular plant species as a genotyping tool (Elshire et al., *PloS One*, 6 (5): e19379, 2011; Poland et al., *PloS One*, 7 (2): e32253, 2012; Truong et al., *PloS One* 7 (5): e37565, 2012). High-throughput sequencing platforms are known in the art and any such high-throughput sequencing platform may be used according to the methods of the present invention. Non-limiting examples of which include next generation sequencing, single molecule sequencing, and nanopore sequencing. In certain embodiments, a method of determining a genotype may include genetic fingerprinting of seeds, plants, or plant parts. Methods of genetic fingerprinting are known in the art. The data obtained from fingerprinting may then be used, in particular embodiments, to select genetic markers, which when used alone and/or in combination, are able to identify or select for certain traits or polymorphisms of onion hybrid SVNT4677 or progeny thereof. In some embodiments, DNA fingerprinting may refer to any laboratory technique known in the art which may be used to determine the probable identity of a plant genotype based on the nucleotide sequences of certain regions of DNA that may be unique to the genotype. In some embodiments, a polymorphism or a plurality of polymorphisms may be detected when the genotype or a sequence of a plant of interest is compared to the genotype or a sequence of one or more reference plants. In certain embodiments, a reference plant may be any plant having a different genotype or sequence compared to the genotype or sequence of the plant of interest. Non-limiting examples of plants that may be utilized as a reference plant include a plant of a parental line and a plant of a related variety or species. In particular embodiments, the genotype or sequence of the reference plant may include, but is not limited to, the genome sequence, or a portion thereof, of a parental line, the genome sequence, or a portion thereof, of a related plant variety or species, a de novo assembled genome sequence, or a portion thereof of a parental line, or a de novo assembled genome sequence, or a portion thereof, of a related plant variety or species.

In certain aspects, the present invention provides a method of determining the genotype of a plant comprising at least a first set of chromosomes of onion hybrid SVNT4677 or a progeny thereof, or a part thereof, the method comprising detecting at least a first polymorphism in a sample of nucleic acids from the plant or part thereof. In one embodiment, the detecting comprises DNA sequencing or genetic marker analysis. In some aspects, the present invention provides a method of determining the genotype of a plant comprising at least a first set of chromosomes of onion hybrid SVNT4677 or a progeny thereof, or a part thereof, the method comprising detecting at least a first polymorphism in a set of the chromosomes of onion hybrid SVNT4677 or progeny thereof. In one embodiment, the present invention provides a method of determining the genotype of a plant comprising at least a first set of chromosomes of onion hybrid SVNT4677 or a progeny thereof, or a part thereof, the method comprising comparing at least a first nucleotide sequence obtained from the plant or part thereof to at least a first reference nucleotide sequence obtained from a reference plant; and detecting at least one polymorphism between the first nucleotide sequence and the first reference sequence. The methods of the present invention may, in certain embodiments, comprise detecting a plurality of polymorphisms as described herein. The method may further comprise, in some embodiments, storing the results of the step of detecting the at least one polymorphism or the plurality of polymorphisms on a computer readable medium or transmitting the results of detecting the at least one polymorphism or the plurality of polymorphisms. The present invention further provides, in particular embodiments, a computer readable medium produced by the methods of the present invention. In some embodiments, a polymorphism or plurality of polymorphisms detected may be indicative of or result in the expression of the morphological and physiological characteristics of onion hybrid SVNT4677 or a progeny thereof.

As used herein, "polymorphism" refers to the presence of one or more variations of a nucleic acid sequence at one or more loci in a population of one or more individuals. The variation may comprise but is not limited to one or more base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (Indels), simple sequence repeats of DNA sequence (SSRs) a restriction fragment length polymorphism, and a tag SNP. A genetic marker, a gene, a DNA-derived sequence, a haplotype, an RNA-derived sequence, a promoter, a 5' untranslated region of a gene, a 3' untranslated region of a gene, microRNA, siRNA, a QTL, a satellite marker, a transgene, mRNA, ds mRNA, a transcriptional profile, and a methylation pattern may comprise polymorphisms.

In certain embodiments, information regarding a polymorphism or a plurality of polymorphisms of the present invention may be stored or provided in a variety of mediums. Non-limiting examples of such mediums include a database and a computer readable medium. In some embodiments, the medium may also contain descriptive annotations in a form that allows a skilled artisan to examine or query the polymorphism or plurality of polymorphisms and obtain useful information.

As used herein "database" refers to any representation of retrievable collected data including computer files such as text files, database files, spreadsheet files and image files, printed tabulations and graphical representations and combinations of digital and image data collections. In one aspect of the present invention a database refers to a memory system that may store computer searchable information.

As used herein, a "computer readable medium" refers to any medium that may be read and/or accessed directly by a computer. Non-limiting examples of a computer readable medium include a magnetic storage medium, such as a floppy disc, a hard disc, a storage medium and magnetic tape; an optical storage media, such as a CD-ROM, an electrical storage medium, such as RAM, DRAM, SRAM, SDRAM, ROM; and PROMs (EPROM, EEPROM, Flash EPROM), and any hybrid of these, such as magnetic/optical storage media. Any computer readable medium known in the art may be used to create a computer readable medium comprising information regarding a polymorphism or a plurality of polymorphisms of the present invention.

As used herein, the term "recorded" refers to the result of a process for storing information in a database or a computer readable medium. A skilled artisan may readily adopt any of the presently known methods for recording information on computer readable medium to generate a computer readable medium comprising information regarding a polymorphism or a plurality of polymorphisms of the present invention. A variety of data storage structures are known in the art and are available to a person of ordinary skill in the art for creating such a computer readable medium. The choice of the data storage structure will generally be based on the means chosen to access the stored information. In addition, a variety of data processor programs and formats may be used to store information regarding a polymorphism or a plurality of polymorphisms of the present invention on a computer readable medium.

The present invention, in certain aspects, further provides systems, particularly computer-based systems, which contain information regarding a polymorphism or a plurality of polymorphisms of the present invention. Such computer-based systems are designed, in certain embodiments, to identify the polymorphisms of the present invention. As used herein, "a computer-based system" refers to the hardware, software, and memory used to analyze a polymorphism or a plurality of polymorphisms. Any computer-based system known in the art may be suitable for use according to the present invention.

G. DEFINITIONS

In the description and table herein, a number of terms are used. In order to provide a clear and consistent understanding of the specification and claims, the following definitions are provided:

Allele: Any of one or more alternative forms of a genetic locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions or transgenes from one genetic background into another.

Crossing: The mating of two parent plants.

Cross-pollination: Fertilization by the union of two gametes from different plants.

Diploid: A cell or organism having two sets of chromosomes.

Elite Variety: Any variety that has resulted from breeding and selection for superior agronomic performance.

Elite Plant: A plant belonging to an elite variety.

Emasculate: The removal of plant male sex organs or the inactivation of the organs with a cytoplasmic or nuclear genetic factor or a chemical agent conferring male sterility.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Progeny: A descendant or descendants of a plant, developed as a result of the breeding of two individual plants or from selfing. The two individual plants used for breeding may be plants of the same genotype or may be plants of two distinct genotypes. During selfing, in some embodiments, the same plant may act as the donor of both male and female gametes. A descendant may be, for example, an $F_1$ generation, an $F_2$ generation, or any subsequent generation seed or plant, or part thereof.

Quantitative Trait Loci (QTL): Quantitative trait loci (QTL) refer to genetic loci that control to some degree numerically representable traits that are usually continuously distributed.

Regeneration: The development of a plant from tissue culture.

Resistance: As used herein, the terms "resistance" and "tolerance" are used interchangeably to describe plants that show no symptoms to a specified biotic pest, pathogen, abiotic influence or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

Royal Horticultural Society (RHS) Color Chart Value: The RHS Color Chart is a standardized reference which allows accurate identification of any color. A color's designation on the chart describes its hue, brightness, and saturation. A color is precisely named by the RHS Color Chart by identifying the group name, sheet number, and letter, e.g., Yellow-Orange Group 19A or Red Group 41B.

Self-pollination (selfing): The transfer of pollen from the anther of a plant to the stigma of the same plant or to the stigma of another plant of the same genotype.

Single Locus Converted (Conversion) Plant: Plants which are developed by a plant breeding technique called backcrossing or genetic engineering of a locus wherein essentially all of the physiological and morphological characteristics of an onion variety are recovered in addition to the characteristics of the single locus.

Substantially Equivalent: A characteristic that, when compared, does not show a statistically significant difference (e.g., $p=0.05$) from the mean.

Tetraploid: A cell or organism having four sets of chromosomes.

Tissue Culture: A composition comprising isolated cells of the same or a different type or a collection of such cells organized into parts of a plant.

Transgene: A genetic locus comprising a sequence which has been introduced into the genome of an onion plant by transformation or site specific modification.

H. DEPOSIT INFORMATION

A deposit of at least 625 seeds of onion hybrid SVNT4677, disclosed above and recited in the claims, has been made with the Provasoli-Guillard National Center for Marine Algae and Microbiota (NCMA), 60 Bigelow Drive, East Boothbay, Maine, 04544 USA. The date of deposit for those deposited seeds is Nov. 21, 2024. The accession number for those deposited seeds of onion hybrid SVNT4677 is NCMA Accession Number 202411020. Upon issuance of a patent, all restrictions upon the deposit will be removed and the deposit is intended to meet all of the requirements of 37 C.F.R. §§ 1.801-1.809. The deposit has been accepted under the Budapest Treaty and will be maintained in the depository for a period of 30 years, or 5 years after the last request, or the effective life of the patent, whichever is longer, and will be replaced if necessary during that period.

EXAMPLES

Example 1. Testing for *Stemphylium* Leaf Blight Resistance in Onion

Resistance to *Stemphylium vesicarium*, the pathogen that causes *Stemphylium* leaf blight (SLB) was evaluated using the pathology assay described herein.

*Stemphylium vesicarium* isolates were maintained as a conidial suspension on silica gel stored at 4° C. To prepare for the resistance assay, the conidial suspension was placed on V8 agar (200 ml of V8 juice in 800 ml of distilled water and 3.6 g of calcium carbonate) by shaking the silica gel crystals onto the solid media. The plates with pathogen were incubated at 24° C. with a 12-hour light/dark cycle for 7 days. The conidial suspension was collected by tilting the plate on one side and gently mixing with a wire loop. To increase the inoculum recovery, the plates were flooded with sterile reverse osmosis water to help dislodge the conidia and were removed by gently scraping off the media with a sterile wire loop. A volume of 200-ul of conidial mixture was recovered and plated onto a fresh V8 agar plate. The conidia were spread across the plate using a sterile L-glass rod. The pathogen plated on V8 agar was grown at 24° C. with a 12-hour light period for 4-5 days. Before harvesting the conidia, the mycelial growth was gently scraped with a sterile microscope slide and the plate was left open for 24 hours at room temperature. Then the plate was covered and left at room temperature for another 24 hours. The conidia were harvested by adding enough water to cover the fungal growth and gently scraping with a sterile slide. The conidial suspension was poured into 2 layers of cheesecloth to remove mycelia and agar fragments. Before using, the conidial suspension was diluted to a concentration of 1×105 conidia/ml, 0.01% Tween20 was added and the suspension was gently agitated to mix the contents.

To assay for resistance, plants were grown for 8 weeks after sowing and subsequently inoculated with the conidial suspension using a spray boom with 4 nozzles at 25 psi. Plants were inoculated 3 times at weekly intervals. After each inoculation, leaves were dried and plants were moved to the humidity tent where 100% relative humidity was maintained for 48 hours. The temperature condition during the bioassay was maintained as 28° C. during day/21° C. during night. The light conditions were maintained for 10 hours light per day. Plants were pruned four inches 2-3 times as needed to prevent lodging, with the last pruning at least 10 days prior to inoculation. One week after inoculation, the disease severity was ranked using a scale from 1 to 9, with 1 being the most resistant and 9 the most susceptible.

Example 2. Identification and Validation of a Novel Allele Conferring Resistance to Stemphylium Leaf Blight The source for this novel resistance allele was identified in an internal onion line (designated SHSLB38B) through a genome-wide association study (GWAS). The panel, consisting of 147 parental lines, was genotyped with 120 markers and phenotypically assayed for resistance to Stemphylium vesicarium according to the protocol described in Example 1 above. In the GWAS model, a correction for population structure was included, and markers were fitted simultaneously.

The validation of the novel resistance allele was performed using $F_2$ populations to evaluate the reaction levels between marker genotypes. Plants that are heterozygous for the favorable allele have a lower average SLB disease score than plants that are homozygous for the non-favorable allele. Plants that are homozygous for the favorable allele have a lower average SLB disease score than plants that are heterozygous or homozygous for the non-favorable allele. It was therefore observed that that resistance allele acts in additive manner, in that the resistance is higher in plants that are homozygous for the favorable allele. Onion hybrid SVNT4677, which has line SHSLB38B as a parent is heterozygous for the favorable allele.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

What is claimed is:

1. An onion plant of onion hybrid SVNT4677, a sample of seed of said hybrid having been deposited under NCMA Accession Number 202411020.

2. An onion seed that produces the plant of claim 1.

3. A plant part of the plant of claim 1, wherein the plant part comprises a cell of said plant.

4. An onion plant having all of the physiological and morphological characteristics of the plant of claim 1.

5. A tissue culture of regenerable cells of the plant of claim 1.

6. An onion plant regenerated from the tissue culture of claim 5, wherein said plant has all of the physiological and morphological characteristics of onion hybrid SVNT4677.

7. A method of vegetatively propagating the plant of claim 1, the method comprising the steps of:
    (a) collecting tissue capable of being propagated from the plant of claim 1; and
    (b) propagating an onion plant from the tissue.

8. A method of producing an onion plant comprising an added trait, the method comprising introducing a transgene conferring the trait into the plant of claim 1.

9. An onion plant produced by the method of claim 8, wherein said plant comprises the transgene and otherwise comprises all of the morphological and physiological characteristics of onion hybrid SVNT4677.

10. An onion plant of onion hybrid SVNT4677, a sample of seed of said hybrid having been deposited under NCMA Accession Number 202411020, further comprising a transgene.

11. The plant of claim 10, wherein the transgene confers a trait selected from the group consisting of male sterility, herbicide tolerance, insect resistance, pest resistance, disease resistance, modified fatty acid metabolism, environmental stress tolerance, modified carbohydrate metabolism, and modified protein metabolism.

12. An onion plant of onion hybrid SVNT4677, a sample of seed of said hybrid having been deposited under NCMA Accession Number 202411020, further comprising a single locus conversion.

13. The plant of claim 12, wherein the single locus conversion confers a trait selected from the group consisting of male sterility, herbicide tolerance, insect resistance, pest resistance, disease resistance, modified fatty acid metabolism, environmental stress tolerance, modified carbohydrate metabolism, and modified protein metabolism.

14. A method for producing a seed of an onion plant derived from onion hybrid SVNT4677, the method comprising the steps of:
    (a) crossing the plant of claim 1 with itself or a different onion plant; and
    (b) allowing a seed of an onion hybrid SVNT4677-derived onion plant to form.

15. A method of producing a seed of an onion hybrid SVNT4677-derived onion plant, the method comprising the steps of:
    (a) producing an onion hybrid SVNT4677-derived onion plant from a seed produced by crossing the plant of claim 1 with itself or a different onion plant; and (b) crossing the onion hybrid SVNT4677-derived onion plant with itself or a different onion plant to obtain a seed of a further onion hybrid SVNT4677-derived onion plant.

16. The method of claim 15, the method further comprising producing an onion plant grown from the seed of said step (b) and crossing said onion plant with itself or a different onion plant to produce a seed of an onion hybrid SVNT4677-derived onion plant.

17. A method of producing onions comprising:
(a) obtaining the plant of claim 1, wherein the plant has been cultivated to maturity, and
(b) collecting at least one onion from the plant.

18. A method of determining the genotype of the plant of claim 1 or a progeny plant thereof, or a part thereof, the method comprising detecting at least a first polymorphism in a sample of nucleic acids from said plant or part thereof.

19. The method of claim 18, wherein said detecting comprises DNA sequencing or genetic marker analysis.

20. The method of claim 18, the method further comprising storing the results of said detecting on a computer readable medium or transmitting the results of the detecting.

21. An onion plant comprising a *Stemphylium* leaf blight (SLB) resistance allele that confers to said plant an increased resistance to SLB compared to a plant not comprising said allele, wherein said allele is inherited from a plant of onion hybrid SVNT4677 or a progeny plant thereof, a sample of seed of said hybrid having been deposited under NCMA Accession Number 202411020.

22. The onion plant of claim 21, wherein said plant is a hybrid onion plant or an inbred onion plant.

23. An onion seed that produces the plant of claim 21.

24. A plant part of the plant of claim 21, wherein the plant part comprises a cell of said plant.

25. A tissue culture of regenerable cells of the plant of claim 21.

26. A method of vegetatively propagating an onion plant, the method comprising the steps of:
(a) collecting tissue capable of being propagated from the plant of claim 21; and
(b) propagating an onion plant from the tissue.

27. A method of producing onions comprising:
(a) obtaining the plant of claim 21, wherein the plant has been cultivated to maturity, and
(b) collecting at least one onion from the plant.

* * * * *